United States Patent [19]
Griffith

[11] Patent Number: 5,158,883
[45] Date of Patent: Oct. 27, 1992

[54] METHOD OF USING AMINOARGININE TO BLOCK NITRIC OXIDE FORMATION IN VITRO

[75] Inventor: Owen W. Griffith, New York, N.Y.

[73] Assignee: Cornell Research Foundation, Inc., Ithaca, N.Y.

[21] Appl. No.: 672,030

[22] Filed: Mar. 19, 1991

Related U.S. Application Data

[62] Division of Ser. No. 406,897, Sep. 13, 1989, Pat. No. 5,059,712.

[51] Int. Cl.$^5$ ............................................. C12N 5/06
[52] U.S. Cl. ................................. 435/240.2; 435/114; 514/565
[58] Field of Search ............. 435/240.2, 240.3, 240.31, 435/114; 514/565

[56] References Cited

U.S. PATENT DOCUMENTS

| | | | |
|---|---|---|---|
| 4,282,217 | 8/1981 | Baglioni | 514/179 |
| 4,698,442 | 10/1987 | Nestor et al. | 562/560 |
| 5,028,627 | 7/1991 | Kilbourn et al. | 514/565 |

OTHER PUBLICATIONS

Natanson, C., et al., Journal of Exp. Med. 169:823–832 (1989).
Hibbs, J. B., et al., Biochem. Biophys. Res. Commun. 157:87–94 (1988).
Marletta, M. A., et al., Biochemistry 27:8706–8711 (1988).
Palmer, R. M. J., et al., Nature 327:524–526 (1987).
Aisaka, K., et al., Biochemical and Biophysic Research Communications, vol. 160, No. 2, pp. 881–886, Apr. 28, 1989.
Iyengar, R., et al., Proc. Natl. Acad. Sci, USA, vol. 84, pp. 6369–6373 Sep. 1987.
Palmer, R. M. J., et al., Nature (London), 333, pp. 664–666, 1988.
Rees, D. D., et al., Proc. Natl. Acad. Sci. USA, vol. 86, pp. 3375–3378, May 1989.
Palmer, R. M. J., et al., Biochem and Biophysical Research Communications, 153, No. 3, 1251–1256 (Jun. 1988).
Steuhr, D. J., et al., The Journal of Immunology, 139, No. 2, 518–525, (1987).
Schmidt, H. H. H. W., et al., European Journal of Pharmacology, 154, 213–216, (1988).
Steuhr, D. J., et al., J. Exp. Med. vol. 169, pp. 1011–1020 (Mar. 1989).
Stuehr, D. J., et al., J. Biochem. and Biophysical Research Communications, vol. 161, No. 2, pp. 420–426 (Jun. 15, 1989).
Turan, A., et al., Acta Chimica Academiae Scientiarum Hungaricae, Tomus 85 (3), pp. 327–332 (1975).
Kilbourn, R. G., et al., Proc. Natl. Acad. Sci. USA vol. 87, pp. 3629–3632, May 1990.
Sakuma, I., et al., Proc. Natl. Acad. Sci. USA vol. 85, pp. 8664–8667, Nov. 1988.

*Primary Examiner*—Douglas W. Robinson
*Assistant Examiner*—Marian C. Knode

[57] ABSTRACT

Pharmaceutically pure physiologically active $N^G$-aminoarginine (i.e., the L or D,L form) or pharmaceutically acceptable salt thereof is administered in a nitric oxide synthesis inhibiting amount to a subject in need of such inhibition (e.g. a subject with low blood pressure or needing immunosuppressive effect) or is added to a medium containing isolated organs, intact cells, cell homogenates or tissue homogenates in an amount sufficient to inhibit nitric oxide formation to elucide or control the biosynthesis, metabolism or physiological role of nitric oxide.

$N^G$-amino-L-arginine is prepared and isolated as a pharmaceutically pure compound by reducing $N^G$-nitro-L-arginine, converting L-arginine by-product to L-ornithine with arginase and separating $N^G$-amino-L-arginine from the L-ornithine. $N^G$-amino-D,L-arginine is prepared in similar fashion starting with $N^G$-nitro-D,L-arginine.

1 Claim, No Drawings

METHOD OF USING AMINOARGININE TO BLOCK NITRIC OXIDE FORMATION IN VITRO

This invention was made at least in part with Government support under National Institutes of Health grant number DK 37116. The Government has certain rights in the invention.

This is a divisional of copending application Ser. No. 07/406,897, filed Sep. 13, 1989, now U.S. Pat. No. 5,059,712.

TECHNICAL FIELD

This invention is directed to novel inhibitors of biological nitric oxide formation.

BACKGROUND OF THE INVENTION

For several decades nitroglycerin has been administered to humans as a vasodilating agent in the treatment of cardiovascular disease. Recently, it has been shown that nitroglycerin so administered is converted in the body to nitric oxide which is the pharmacologically active metabolite. Still more recently, nitric oxide has been shown to be formed from arginine as a normal metabolite which is an important component of endothelium-derived relaxing factors (EDRF's). EDRF's are currently being intensively studied as participating in regulation of blood flow and vascular resistance. Incident to such study, a search has been carried out for compounds which block nitric oxide production in the body. The compound discovered for use to obtain this effect is $N^G$-methyl-L-arginine (Palmer, R. M. J., et al, *Nature* (London), 333, pp. 664–666, 1988). Administration of $N^G$-methyl-L-arginine to guinea pigs and rabbits has been shown to increase blood pressure (Aisaka, K., et al, *Biochemical and Biophysic Research Communications*, Vol. 160, No. 2, pp. 881–886, 4/28/89; Rees, D. D., et al, *Proc. Natl. Acad. Sci.* USA, Vol. 86, pp. 3375–3378, 5/89).

In addition to vascular endothelium, macrophages have also been shown to produce nitric oxide in the body which is a component of their cell killing and/or cytostatic function (Iyengar, R., et al, *Proc. Natl. Acad. Sci.* USA, Vol. 84, pp. 6369–6373, 9/87).

SUMMARY OF THE INVENTION

It has been discovered herein that physiologically active $N^G$-aminoarginine (wherein the terminology $N^G$ indicates substitution on a guanidino nitrogen) and its pharmaceutically acceptable acid addition salts constitute superior inhibitors of nitric oxide synthesis in the body. The term physiologically active $N^G$-aminoarginine is used herein to mean $N^G$-aminoarginine selected from the group consisting of $N^G$-amino-L-arginine and $N^G$-amino-D,L-arginine. In the D,L-compound only the $N^G$-amino-L-arginine portion is physiologically active.

$N^G$-amino-L-arginine has been reported as a by-product in the reductive deprotection of $N^G$-nitro-L-arginine which is used in chemical synthesis of peptides. However, no report is known of the preparation and isolation of such or of $N^G$-amino-D,L-arginine in pharmaceutically pure form. The invention herein contemplates such preparation and isolation.

Thus composition herein which is considered to be novel is pharmaceutically pure physiologically active $N^G$-aminoarginine or a pharmaceutically acceptable acid addition salt thereof. The term pharmaceutically pure is used herein to mean 99.9+% pure (on a water-free basis).

The method of the invention herein for preparing and isolating physiologically active $N^G$-aminoarginine comprises the steps of:

(a) reducing $N^G$-nitro-L-arginine or $N^G$-nitro-D,L-arginine to form a mixture of physiologically active $N^G$-aminoarginine and arginine;

(b) treating said mixture with arginase to convert the arginine therein to ornithine thereby forming a mixture of physiologically active $N^G$-aminoarginine and ornithine;

(c) isolating pharmaceutically pure physiologically active $N^G$-aminoarginine from the mixture resulting from step (b).

The isolation of step (c) is readily carried out by chromatography or by crystallization of the $N^G$-aminoarginine as the flavianic acid salt.

A method herein for inhibiting nitric oxide synthesis in a subject in need of such inhibition comprises administering a nitric oxide synthesis inhibiting amount of physiologically active $N^G$-aminoarginine or pharmaceutically acceptable acid addition salt thereof to said subject. The term "subject" is used herein to mean any mammal, including humans, where nitric oxide formation from arginine occurs. This method contemplates prophylactic as well as curative use.

A method herein for blocking nitric oxide formation from arginine in in vitro studies including studies with isolated organs, intact cells, cell homogenates and tissue homogenates to elucidate or control the biosynthesis, metabolism or physiological role of nitric oxide comprises adding physiologically active $N^G$-aminoarginine or pharmaceutically acceptable acid addition salt thereof to a medium containing said organs, cells, or homogenates at a concentration sufficient to inhibit nitric oxide formation.

DETAILED DESCRIPTION

As previously indicated, inventive composition herein constitutes pharmaceutically pure physiologically active $N^G$-aminoarginine or a pharmaceutically acceptable acid addition thereof.

$N^G$-amino-L-arginine in free base form has the structural formula

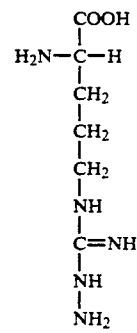

$N^G$-amino-D,L-arginine in free base form consists of 50% $N^G$-amino-L-arginine and 50% $N^G$-amino-D-arginine which has the structural formula:

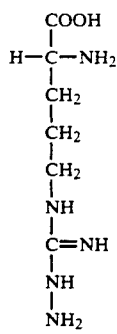

The pharmaceutically acceptable acid addition salts are formed initially at the nitrogen with the higher pKa and include, for example, the hydrochloric acid, sulfuric acid, acetic acid, gluconic acid, phosphoric acid, succinic acid, maleic acid, and citric acid addition salts. These are formed by methods well known in the art.

We turn now to preparing and isolating pharmaceutically pure physiologically active $N^G$-aminoarginine. The $N^G$-nitroarginine starting material is $N^G$-nitro-L-arginine for producing $N^G$-amino-L-arginine and $N^G$-nitro-D,L-arginine for producing $N^G$-amino-D,L-arginine. $N^G$-nitro-L-arginine is readily commercially available. $N^G$-nitro-D,L-arginine is produced the same way as $N^G$-nitro-L-arginine except starting with a D,L-source. When $N^G$-nitro-L-arginine is the starting material, the product of step (a) is a mixture of $N^G$-amino-L-arginine and L-arginine. When $N^G$-nitro-D,L-arginine is the starting material, the product of step (a) is a mixture of $N^G$-amino-D,L-arginine and D,L-arginine. Reduction of $N^G$-nitroarginine is readily carried out by reaction of it in solution with hydrogen gas in excess over a suitable reduction catalyst (e.g., Pt on charcoal, PtO, Pd on charcoal, and others well known in the reduction art). Suitable solvents are aqueous acids, e.g., 15% aqueous acetic acid. The reduction reaction is readily carried out at room temperature but temperatures ranging, for example, from 0° C. to 100° C. or higher can be employed. The reduction reaction proceeds readily at a pressure of 40 psi but can be carried out at pressures ranging from 1 to 2000 psi.

In step (b), L-arginine is converted to L-ornithine or D,L-arginine is converted to D,L-ornithine. For step (b), the step (a) catalyst is removed, e.g., by filtering, and the solvent is removed, e.g., by rotary evaporation at reduced pressure. The resulting residue is dissolved in water and is adjusted to slightly alkaline pH, e.g., pH ranging from 8 to 10 by addition of base, e.g., NaOH. The arginase (which is readily commercially available) is then added at a concentration ranging, for example, from 0.5 to 5 mg per gram of $N^G$-nitroarginine starting material. Reaction is carried out, for example, by incubation for 8–12 hours at 20° to 40° C., preferably overnight at 37° C. On completion of reaction the arginase is removed, e.g., by heat denaturation and centrifugation or filtration, and the resultant product is subject to treatment in step (c).

Chromatographic separation in step (c) is readily effected on strong acid cation exchange resin (e.g., Dowex 50 in hydrogen or sodium form) and elution with moderately to strongly basic solutions, e.g., a gradient formed between water and dilute ammonium hydroxide. Fractions are collected and analyzed by high performance liquid chromatography (hereinafter HPLC). Appropriate fractions are pooled and the ornithine- and arginine-free product isolated, e.g., by rotary evaporation.

Turning now to the embodiment of step (c) involving crystallization of $N^G$-aminoarginine as the flavianic acid salt, this is carried by adding an aqueous solution of flavianic acid (e.g., 6–10 gms/100 ml) until the pH is about 3.8, chilling, for example, to 2°–10° C., and collecting the resulting yellow precipitate, e.g., by filtration. The precipitate is recrystallized preferably by successively raising and lowering the pH with NaOH and HCl and a solution of pharmaceutically pure $N^G$-aminoarginine is produced from the recrystallized flavianic salt by stirring said salt with a suspension of strong base anion exchange resin (e.g., Dowex 1) to bind the flavianic acid and release the $N^G$-aminoarginine. The resin with flavianic acid bound thereto is separated, e.g., by filtering. The pharmaceutically pure physiologically active $N^G$-aminoarginine product is recovered as a solid by evaporating or otherwise drying the filtrate.

We turn now to the in vivo method herein, which comprises administering a nitric oxide synthesis inhibiting amount of physiologically active $N^G$-aminoarginine or acid addition salt thereof to a subject in need of such inhibition.

One group of subjects comprises those with pathologically low blood pressure.

One class within this group are those with idiopathic hypotension.

Another class within this group are those with drug induced hypotension. In this case coadministration pursuant to the method herein allows use of drugs that otherwise have unacceptable side effects.

Still another class within this group are those suffering from shock (including toxic shock syndrome).

Reference is made to an application of Robert G. Kilbourn, Steven S. Gross, Owen W. Griffith and Roberto Levi titled "Inhibition of Systemic Hypotension Produced By Biologic Response Modifiers" filed on Sep. 13, 1989 via the express mail method, U.S. Ser. No. 07/406,909, now U.S. Pat. No. 5,028,627. The Kilbourn et al application embraces use of compounds including those claimed herein in inhibiting systemic hypotension.

Another group of subjects comprises those with immune disorders in which down regulation of nitric oxide formation is advantageous, e.g., in auto-immune disorders or in therapeutic immunosuppression for transplant purposes.

Turning now to dosage, such depends on the effect desired and the responsiveness of the individual subject. For example, for raising blood pressure, a blood pressure effective raising amount is administered. For disorders requiring immunosuppression, an immunosuppressive effective amount is administered. Generally, dosages range from 10 micrograms per kg to 100 mg/kg, preferably 1 to 10 mg/kg are useful. For $N^G$-amino-D,L-arginine, the dosage is twice that for $N^G$-amino-L-arginine.

Administration is readily carried out, for example, by oral or parenteral routes.

The physiologically active $N^G$-aminoarginine is readily administered in combination with typical bulking agents, flavors and the like.

We turn now to the in vitro method herein. Typically media include cardiac perfusion media, tissue culture media, incubation media used with cell or tissue homogenates or purified proteins. The organ treated is typically a blood vessel, lung or kidney. Intact cells include vascular endothelium or macrophages. The homogenates can be, for example, from cardiac, vascular, neural or other tissues and cells. The physiologically active $N^G$-aminoarginine or salt thereof is added to the medium, in a concentration ranging from 1 nanomolar to 300 millimolar.

The invention is illustrated in the following examples.

EXAMPLE I 4.38 (20 mmol) $N^G$-nitro-L-arginine (Sigma Chemicals) was dissolved in 25 ml of 15% aqueous acetic acid with 0.1 gm platinum oxide. The reaction was carried out at 40 psi $H_2$ pressure and room temperature for about 60 hours. Catalyst was removed by filtration under argon, and the filtrate was rotary evaporated under reduced pressure to an oil. The oil was repeatedly dissolved in water and evaporated under vacuum and finally dissolved in 40 ml water. Analysis indicated 55% $N^G$-amino-L-arginine and 45% L-arginine. The solution was adjusted to pH of 9.5 with NaOH and 5 mg arginase was added (1050 IU). The resulting solution was incubated at 37° C. overnight. After this treatment the solution contained $N^G$-amino-L-arginine and L-orthinine but no L-arginine. The arginase was denatured by heating the solution to 100° C. for 5 to 10 minutes and removed by filtration. An aqueous solution of flavianic acid (6.28 gm in 100 ml) was added until the pH was about 3.8 and precipitate began to form. The solution was chilled to 40° C. overnight to complete precipitation of the product and the precipitate was collected by filtration (about 3.0 gm). The solid was redissolved in hot water (100 ml) by dropwise addition of 1M NaOH. Addition to that solution of HCl to pH 3.8 caused formation of crystals of $N^G$-amino-L-arginine monoflavianic acid salt. After chilling of the solution at 4° C. for 4 hours, the yellow crystals were collected by filtration and washed sequentially with absolute ethanol and ethyl ether. The product (2.4 grams) was pure $N^G$-amino-L-arginine monoflavianic acid salt ($C_{16}H_{21}N_7O_{10}S$ requires: C=38.2%; H=4.2%; N=19.5%. Found: C=38.4%, H=4.2%; N=19.5%). The monoflavianic acid salt was suspended in 100 ml of water at 100° C. and 10 grams of Dowex 1 (OH$^-$), a strong base ion exchange resin, was added. After stirring at 100° C. for 5 hrs the supernatant was clear and all of the yellow flavianic acid was bound to the Dowex 1 resin. The resin was removed by filtration, and the clear filtrate was dried to an oil by rotary evaporation at reduced pressure. The oil was dissolved in 50 ml of ethanol and the ethanol was evaporated at reduced pressure. Addition and removal of ethanol was repeated again, and then 50 ml of ethyl ether was similarly added and removed. The solid residue was dried under high vacuum over $P_2O_5$ for 12 hours. The yield was 1.2 grams of pure (99.9+% pure) $N^G$-amino-L-arginine (35% yield based on starting $N^G$-nitro-L-arginine).

EXAMPLE II $N^G$-nitro-L-arginine (4.38 gm) was reduced to a mixture of L-arginine and $N^G$-amino-L-arginine and treated with arginase as described in Example I. The arginase-free solution was evaporated to dryness and the dried residue was dissolved in 10 ml of water and the resulting solution was applied to a column (2.5×45 cm) of Dowex 50 (H$^+$) resin. The resin was washed with water (500 ml) and then with a linear gradient formed between 1 liter of water and 1 liter of 2M ammonium hydroxide. Fractions of 25 ml were collected and analyzed for their content of ornithine and/or $N^G$-amino-L-arginine. Fractions containing pure $N^G$-amino-L-arginine were pooled and rotary evaporated to dryness at reduced pressure. The semicrystalline residue was dried under vacuum over $P_2O_5$. After drying, the white solid (1.5 gms) was 99.9+% pure $N^G$-amino-L-arginine

EXAMPLE III

A male Hartley guinea pig weighing 500 grams is anesthetized with sodium pentobarbital (50 mg/kg i.p.) and a tracheal cannula is inserted. The left carotid artery is cannulated and connected to a physiological pressure transducer. Blood pressure tracings are displayed on a physiograph. Diastolic blood pressure is monitored following intravenous administration of saline, $N^G$-methyl-L-arginine (0.1, 1 or 10 mg/kg body weight) or $N^G$-amino-L-arginine (0.1, 1 or 10 mg/kg body weight). A separate guinea pig is used for each compound. Five minutes after drug administration, saline and 0.1 mg/kg $N^G$-methyl-L-arginine has no effect on blood pressure whereas 1 mg/kg and 10 mg/kg $N^G$-methyl-L-arginine increased blood pressure 10 and 25 mm Hg, respectively (Aisaka, K., et al, at page 882 cited above). Five minutes after administration of 0.1, 1 and 10 mg/kg $N^G$-amino-L-arginine diastolic blood pressure increases 10, 20 and 40 mm Hg respectively.

EXAMPLE IV

Vascular relaxation is conveniently studied using isolated rings taken from the aortic or pulmonary vessels of guinea pigs. Addition of acetylcholine to such rings causes synthesis of nitric oxide from L-arginine and the produced nitric oxide causes relaxation of the smooth muscle cells controlling the vascular tone of the vessel ring. Inhibition of nitric oxide formation decreases the relaxant effect of acetylcholine. This in vitro system is a good model for studying chemically induced hypotension due to excessive vascular relaxation.

The effect of $N^G$-amino-L-arginine on the acetylcholine-mediated relaxation of guinea pig aortic and pulmonary rings was determined as described by the method described in Sakuma, I., et al., *Proc. Natl. Acad. Sci. USA* 85, 8664–8667 (1988). The dose of acetylcholine ranged from $10^{-8}$ to $10^{-5}$ M. $N^G$-amino-L-arginine was added at doses of 0, 3 micromolar, 10 micromolar and 30 micromolar. In the absence of $N^G$-amino-L-arginine, acetylcholine at a dose of $10^{-8}$, $10^{-7}$, $10^{-6}$ and $10^{-5}$ M caused a relaxation of about 10%, 23%, 43%, and 58%, respectively. Similar studies in the presence of 3 micromolar $N^G$-amino-L-arginine yielded relaxations of 0%, 0%, 5% and 19%. When the concentration of $N^G$-amino-L-arginine was increased to 10 micromolar or 30 micromolar, the extent of relaxation induced by $10^{-6}$ M acetylcholine was <1% and that caused by $10^{-5}$ M acetylcholine was <10%. Lower doses of acetylcholine did not cause relaxation in the presence of 10 micromolar or 30 micromolar $N^G$-amino-L-arginine. The results show that acetylcholine-mediated vascular relaxation is due in large part to nitric oxide formation from L-arginine and is inhibited by $N^G$-amino-L-arginine. Since such study is a good model for in vivo hypotension, the results also indicate in vivo utility of $N^G$-amino-L-arginine in raising low blood pressure due to nitric oxide medicated vascular relaxation.

In similar studies, $N^G$-methyl-L-arginine was required at concentrations about 5 to 10 fold higher than the listed doses of $N^G$-amino-L-arginine to cause comparable inhibition of vascular ring relaxation.

When equimolar amounts of $N^G$-nitro-D,L-arginine are substituted for the $N^G$-nitro-L-arginine in Examples I or II, pure $N^G$-amino-D,L-arginine is obtained.

When in Examples III and IV, $N^G$-amino-D,L-arginine is substituted for $N^G$-amino-L-arginine in twice the dosage or concentration, substantially equal results of diastolic blood pressure increase and inhibition of vascular ring relaxation are obtained.

Many variations of inventive embodiments will be obvious to those skilled in the art. Thus, the inventive embodiments are defined by the claims.

What is claimed is:

1. A method for controlling the biosynthesis, metabolism or physiological role of nitric oxide in vitro, comprising adding physiologically active $N^G$-aminoarginine or a pharmaceutically acceptable acid addition salt thereof to a medium containing isolated organs, intact cells, cell homogenates or tissue homogenates from mammals at a concentration sufficient to inhibit nitric oxide formation from arginine.

* * * * *